(12) United States Patent  
Alkhatib

(10) Patent No.: US 8,597,349 B2  
(45) Date of Patent: Dec. 3, 2013

(54) COLLAPSIBLE/EXPANDABLE PROSTHETIC HEART VALVES WITH NON-EXPANDING STENT POSTS AND RETRIEVAL FEATURES

(75) Inventor: Yousef F. Alkhatib, Edina, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 69 days.

(21) Appl. No.: 12/733,761

(22) PCT Filed: Nov. 3, 2008

(86) PCT No.: PCT/US2008/012437  
§ 371 (c)(1),  
(2), (4) Date: Mar. 18, 2010

(87) PCT Pub. No.: WO2009/061389  
PCT Pub. Date: May 14, 2009

(65) Prior Publication Data  
US 2010/0249911 A1    Sep. 30, 2010

Related U.S. Application Data

(60) Provisional application No. 61/001,976, filed on Nov. 5, 2007.

(51) Int. Cl.  
*A61F 2/24* (2006.01)  
*A61F 2/82* (2006.01)

(52) U.S. Cl.  
USPC ........................................................ 623/2.17

(58) Field of Classification Search  
USPC ................................................ 623/1.15–2.19  
See application file for complete search history.

(56) References Cited

U.S. PATENT DOCUMENTS

| 7,618,447 | B2 * | 11/2009 | Case et al. | 623/1.26 |
| 2006/0122692 | A1 | 6/2006 | Gilad et al. | |
| 2007/0100435 | A1 * | 5/2007 | Case et al. | 623/1.24 |
| 2008/0188924 | A1 * | 8/2008 | Prabhu | 623/1.16 |
| 2009/0062904 | A1 * | 3/2009 | Furst | 623/1.15 |

(Continued)

FOREIGN PATENT DOCUMENTS

| EP | 1690515 | | 8/2006 |
| EP | 2205184 | A2 | 7/2010 |

(Continued)

OTHER PUBLICATIONS

PCT International Search Report date Jul. 16, 2009.

(Continued)

*Primary Examiner* — Suzette J Gherbi  
(74) *Attorney, Agent, or Firm* — Lerner, David, Littenberg, Krumholz & Mentlik, LLP

(57) ABSTRACT

A frame structure for a collapsible and re-expandable prosthetic heart valve. The frame structure includes an annular annulus portion that is configured for implanting in or near a patient's native heart valve annulus. This annulus portion of the frame structure may include a plurality of annularly spaced commissure post structures interconnected by connecting structures. The commissure post structures may be more resistant to annular collapse than the connecting structures. In the case of a prosthetic aortic valve, the frame structure may also include an annular aortic portion. The aortic portion may include a plurality of attachment points (for tethers) closest to the annulus portion. Such attachment points and tethers can facilitate re-collapse of a partly deployed valve in the event of a need to reposition or remove the valve.

13 Claims, 13 Drawing Sheets

(56) References Cited

U.S. PATENT DOCUMENTS

2009/0248139 A1* 10/2009 Pellegrini .................... 623/1.17
2011/0098800 A1* 4/2011 Braido et al. ................ 623/1.16
2011/0208290 A1* 8/2011 Straubinger et al. ......... 623/1.15

FOREIGN PATENT DOCUMENTS

| WO | 2005046528 A1 | 5/2005 |
|---|---|---|
| WO | 2005062980 A2 | 7/2005 |
| WO | 2008010817 A1 | 1/2008 |
| WO | 2008029296 A2 | 3/2008 |
| WO | WO2008/150529 | 12/2008 |
| WO | 2009029199 A1 | 3/2009 |
| WO | 2009045334 A1 | 4/2009 |
| WO | 20091045338 A1 | 4/2009 |
| WO | 2009061389 A2 | 5/2009 |

OTHER PUBLICATIONS

U.S. Appl. No. 61/001,176, filed Novmber 5, 2007.
Opposition against European patent EP2205184B1 dated Mar. 28, 2012.

* cited by examiner

US 8,597,349 B2

COLLAPSIBLE/EXPANDABLE PROSTHETIC HEART VALVES WITH NON-EXPANDING STENT POSTS AND RETRIEVAL FEATURES

This application claims the benefit of U.S. provisional patent application No. 61/001,976, filed Nov. 5, 2007, which is hereby incorporated by reference herein in its entirety.

BACKGROUND OF THE INVENTION

This invention relates to prosthetic heart valves of the kind that can be collapsed to a reduced circumferential size for delivery to the valve-implant site in a patient (e.g., in or through the lumen of tubular delivery apparatus such as a catheter, a trocar, laparoscopic apparatus, or the like). When the valve is at the implant site, it can be released from the delivery apparatus, which allows the valve to re-expand (or to be re-expanded) to its larger, full, operational, circumferential size. This re-expansion may be wholly elastic, wholly plastic, or partly elastic and partly plastic. Elastic re-expansion may be achieved by using a springy metal such as nitinol in the valve. Plastic expansion may be achieved, for example, by inflating a balloon inside the valve. In addition to restoring the valve to the size that permits it to operate as a valve (i.e., a size at which the flexible leaflets in the valve can open and close), re-expansion of the valve causes the valve to engage native tissue of the patient at the implant site, thereby anchoring the valve at that location in the patient.

Terms like retrieval, repositioning, and removal refer to the ability to return the valve to the delivery apparatus after it has wholly or partly left that apparatus. Such retrieval may be done to allow the valve to be moved to another, different location or orientation in the patient (so-called repositioning), or to completely remove the valve from the patient (so-called removal). Returning the valve to the delivery apparatus involves re-collapsing the valve to its reduced circumferential size. If the valve is to be repositioned, then when the valve is at the desired new location or orientation in the patient, the valve leaves the delivery apparatus again, and it again expands (or is expanded) to its full operating size.

There are many considerations involved in designing a prosthetic heart valve that can collapse to a relatively small diameter without, for example, damaging the flexible leaflets of the valve, and that can also be re-collapsed (e.g., for repositioning) after expansion or partial expansion at the implant site in the patient. There is therefore an on-going need for improvements in these and other areas of prosthetic heart valve design.

SUMMARY OF THE INVENTION

In accordance with certain possible aspects of the invention, a frame structure for a prosthetic heart valve may include a plurality of Y-shaped structures disposed in an annular array in which the Y-shaped structures are spaced from one another in a direction that is annular of the array. For example, each of the Y-shaped structures may provide a commissure post region of the prosthetic valve. Each of the Y-shaped structures may include a base member having a first free end portion (providing, for example, a commissure post tip of the prosthetic valve) and an opposite second end to which a first end of each of two arms of the Y-shaped structure are connected. The arms of each of the Y-shaped structures diverge from one another in a direction away from the second end of the associated base member to define an annular space between the arms. The frame structure may further include a plurality of connecting structures, each of which extends between a respective pair of annularly adjacent ones of the Y-shaped structures, and each of which interconnects the Y-shaped structures in the associated pair. Each of the connecting structures may be collapsible and re-expandable in the annular direction. Each of the Y-shaped structures is preferably sufficiently strong to maintain at least 75% of the space between its arms when the array is subjected to an annular collapsing force that collapses it to 50% of an initial annular size.

In accordance with another possible aspect of the invention, each of the above-mentioned connecting structures may be connected to the arms of the above-mentioned Y-shaped structures in the associated pairs but not to the base members of those Y-shaped structures.

In accordance with yet another possible aspect of the invention, each of the above-mentioned Y-shaped structures may further include a linking member that interconnects the arms of that Y-shaped structure at a location that is spaced from the second end of the base member of that Y-shaped structure.

In accordance with still another possible aspect of the invention, the above-mentioned array may lie in an approximately tubular geometric space that surrounds a central longitudinal axis. The base member of each of the above-mentioned Y-shaped structures may be approximately parallel to this longitudinal axis. All of the above-mentioned first free end portions may point in a first direction along this longitudinal axis. The first free end portions may all extend farther in the first direction than any portions of any of the above-mentioned connecting structures.

In accordance with yet another possible aspect of the invention, no portions of any of the above-mentioned Y-shaped structures may extend as far opposite the above-mentioned first direction as portions of the above-mentioned connecting structures. Again, in such a case, each of the Y-shaped structures may further include a linking member that interconnects the arms of that Y-shaped structure at a location that is spaced from the second end of the base member of that Y-shaped structure. Alternatively, when such linking members are provided, the linking member of each of the Y-shaped structures may extend approximately as far opposite the first direction as portions of the connecting structures.

In accordance with still another possible aspect of the invention, the frame structure may further include an aortic portion that is spaced from the above-mentioned Y-shaped structures and connecting structures in the first direction. The aortic portion may be annular about the above-mentioned longitudinal axis and is annularly collapsible and re-expandable. The frame structure may further include a plurality of strut members for attaching the aortic portion to the Y-shaped and connecting structures of the frame structure. In such a case, the aortic portion may include a plurality of closed-perimeter, open-centered cells disposed in an annular array in which connection points between annularly adjacent cells are at intermediate points along sides of the cells and each cell includes first and second ends that respectively point in the above-mentioned first direction and opposite that first direction. Further in such a case, the second end of each of the cells may include an eyelet or other such feature for attaching a tether member that can be used to pull that eyelet or other such feature radially in toward the above-mentioned central longitudinal axis.

In accordance with yet another possible aspect of the invention, a frame structure for a prosthetic heart valve may include an annulus portion that is annular about a longitudinal axis and that is annularly collapsible and re-expandable. The frame structure may further include an aortic portion that is also annular about the longitudinal axis and that is also annularly collapsible and re-expandable. The frame structure may still further include a plurality of strut members for connecting the annulus portion to the aortic portion at a plurality of points that are spaced from one another in a direction that is annular of the aortic portion. The aortic portion may include, at each of the above-mentioned points, a pair of arm members that begin at that point and that diverge from one another in the first direction with an included angle between the arm members of less than 90°. Each such arm member extends in this fashion from its beginning point until it connects to an annularly adjacent arm member that began from another annularly adjacent one of the above-mentioned beginning points. The aortic portion preferably includes no other structure between annularly adjacent ones of the arm members that thus connect to one another and that start from different ones of the above-mentioned beginning or starting points. Similar principles can be alternatively or additionally applied to the annulus portion of the frame structure.

In accordance with still another possible aspect of the invention, a frame structure as summarized in the preceding paragraph may further include a plurality of closed-perimeter, open-centered cells between the arm members that start from each of the above-mentioned starting points. These cells are preferably configured to allow the included angle between those arm members to collapse and re-expand. In such a case, the frame structure may still further include a plurality of additional closed-perimeter, open-centered cells that are disposed in the above-mentioned first direction from the cells between the arm members and that are connected to the cells between the arm members. The additional cells may form an annular array in which those cells are configured to allow the array to annularly collapse and re-expand.

In accordance with yet another possible aspect of the invention, the annulus portion of a frame structure as summarized in the paragraph prior to the preceding one may include a plurality of annularly spaced commissure posts extending in the above-mentioned first direction. In such a case, the strut members may be grouped in a plurality of pairs, each pair being associated with a respective one of the commissure posts, with that commissure post being between the strut members in the associated pair.

Further features of the invention, its nature and various advantages will be more apparent from the accompanying drawings and the following detailed description.

DETAILED DESCRIPTION

Figure 1:
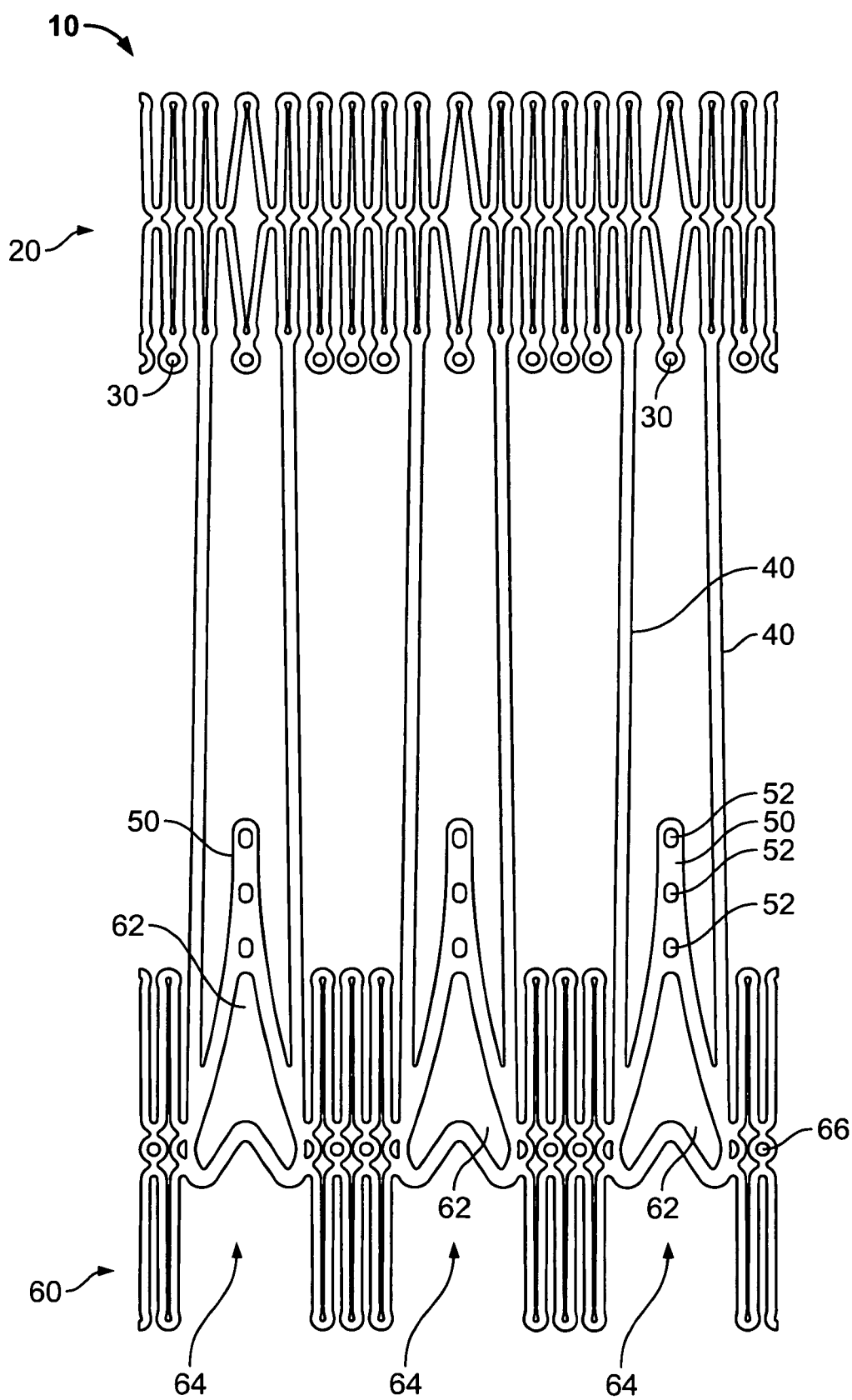
FIG. 1 is a simplified, planar development of an illustrative embodiment of a prosthetic heart valve component in accordance with the invention. By "planar development" it is meant that FIG. 1 shows a component that is actually tubular. But FIG. 1 and other similar FIGS. show this component as though cut along a vertical line and then laid out flat.

All of the FIGS. that accompany this specification show prosthetic aortic valve embodiments. The lower annular part 60 of each of these embodiments is implanted in or near the patient's native aortic valve annulus. Thus the lower annular part 60 may sometimes be referred to as the annulus part or the annulus portion. The upper annular part 20 or 220 of each of these embodiments is implanted in the patient's native aorta, typically downstream (in the direction of blood flow) from the patient's native valsalva sinus. Thus the upper annular part 20 or 220 may sometimes be referred to as the aortic part or the aortic portion. The struts 40 that connect the upper and lower parts of each embodiment typically extend through the patient's native valsalva sinus.

All of the FIGS. that accompany this specification (except for FIG. 3) show the depicted valve component (i.e., frame structure 10, 100, or 200) in the circumferentially (or radially, or annularly, or diametrically) collapsed condition. It will be explained below where in these valve components the expansion occurs when the valve re-expands. All of the FIGS. that accompany this specification omit the flexible valve leaflets that are nevertheless present in valves in accordance with this invention. Examples of how such leaflets may be provided and secured to the components (e.g., frame structure 10, 100, or 200) that are shown in the accompanying FIGS. are shown in Braido U.S. patent application Ser. No. 11/906,133, filed Sep. 28, 2007, which is hereby incorporated by reference herein in its entirety. All of the FIGS. that accompany this specification also omit other components that may be part of valves in accordance with this invention. Examples of such possible other components are tissue layers for cushioning and/or buffering, fabric covers, and the like. (See again the above-mentioned Braido reference.) Some of the accompanying FIGS. show the metal frame component (e.g., 10, 100, or 200) of the valve as though cut along a longitudinal axis and laid out flat. This is only a matter of depiction, however. In all cases the metal frame component 10, 100, or 200 is actually a complete and continuous ring or annular structure, such as is shown in some others of the accompanying FIGS.

The present invention is based on a unique collapsing and expanding frame mechanism concept, several illustrative embodiments of which are shown in the accompanying FIGS. Prosthetic valves in accordance with the invention include such a frame 10, 100, or 200, as well as tissue or polymer valve leaflets (not shown in the accompanying FIGS., as mentioned above). The frame 10, 100, or 200 can be laser-cut from various metals, a particularly preferred metal being nitinol. For example, the starting nitinol metal stock may be a tube. After processing through appropriate annealing steps, the nitinol stent 10, 100, or 200 takes on the final shape and dimensions intended for the final deployment size and shape of patient anatomy. This so-called final shape/dimension is the expanded size of the metal frame 10, 100, or 200, not the collapsed size shown in all of the accompanying FIGS. (with the exception of FIG. 3).

The polymer or tissue valve leaflets (not shown as mentioned above) can be attached to the frame 10, 100, or 200 by various means such as suturing, stapling, or the like. The frame and leaflets (and any other possible components as mentioned above) can then be collapsed in preparation for integration into a delivery system. Various delivery systems can be employed to deliver and deploy the valve at the intended target (implant site) in the patient. The delivery system may depend to some extent on the desired valve implantation approach. Examples of possible approaches are percutaneous retrograde (i.e., percutaneous, meaning catheter-like at least partly through blood vessels of the patient's circulatory system; and retrograde, meaning opposite the blood flow direction), percutaneous antegrade (i.e., antegrade, meaning with the blood flow direction), transapical (i.e., through the apex of the heart), etc. Although the delivery system may thus include certain variations depending on how the implant site is to be approached, all such systems may have similar valve interface mechanisms for collapsing the valve. The valve can be deployed in the same manner for any of the possible approaches, i.e., withdrawal of a sheath that is initially loaded over the collapsed valve to keep the valve in a collapsed state. As the sheath is pulled back, the portions of the stent or frame 10, 100, or 200 that become uncovered by the sheath will start to deploy. The sheath can be pulled in either direction relative to the valve (i.e., either proximally or distally, where proximal means closer to or toward the operator of the delivery apparatus, and distal means farther or away from the operator of the delivery apparatus), but this may also depend on the delivery system design and the approach, as well as on desired performance features. After the valve is fully deployed, the delivery system can still retain the ability recapture the valve for repositioning or retrieval/removal of the valve at the discretion of the operator.

FIG. 1 shows an illustrative embodiment of the metal frame 10 of a prosthetic heart valve in accordance with the invention. As mentioned earlier, FIG. 1 shows frame 10 as though cut longitudinally (i.e., along a vertical axis in FIG. 1) and laid out flat. However, frame 10 is actually a hollow annular (ring-like or tubular) structure in which the left and right edges of what is shown in FIG. 1 are integrally connected to one another. In other words, frame 10 actually forms a continuous, hollow annulus or annular structure (e.g., lying in an approximately tubular geometric space).

In FIG. 1 reference 20 points to the top ring (or aortic portion) cells of frame 10. Eyelets 30 are provided to facilitate stent retrieval with the delivery system. Connecting struts 40 connect top ring 20 to the bottom ring of cells (or annulus portion) 60. Commissure posts 50 project upwardly to some extent from bottom ring 60.

Figure 2:
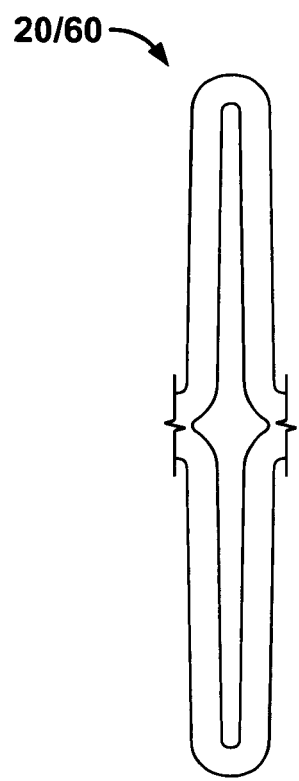
FIG. 2 is a simplified elevational view of a representative portion of the FIG. 1 apparatus in the operating condition of that apparatus that is shown in FIG. 1.
Figure 3:
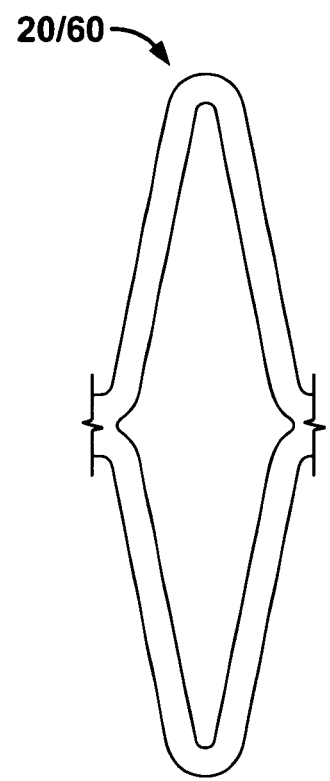
FIG. 3 is a simplified elevational view of the FIG. 2 structure in another operating condition of the apparatus.

FIG. 1 shows a flat development of frame 10 in its annularly compressed or collapsed condition. (Again, such flat depictions of what are actually tube-like structures are employed solely to simplify some of the FIGS. herein.) This is the condition in which closed-perimeter, open-centered cells 20 and 60 are relatively compressed from left to right as viewed in FIG. 1 (see also FIG. 2). A valve may be delivered into a patient in this collapsed condition. FIG. 3 shows what happens to such a representative cell 20/60 (from FIG. 2) when frame 10 expands to the implant and operating condition. Comparison of FIGS. 2 and 3 shows that (in FIG. 3) each cell 20 or 60 becomes much wider in the left-right direction. These increased cell widths add up to make the expanded frame 10 much larger in circumference than the collapsed frame (FIGS. 1 and 2).

It is briefly mentioned again that when the valve is implanted in the patient, top or aortic ring cells 20 are disposed in the patient's aorta (e.g., downstream from the valsalva sinus), connecting struts 40 pass through the valsalva sinus, and bottom or annulus ring cells 60 are disposed in or near the patient's native aortic valve annulus. Commissure posts 50 may be rotationally aligned with the patient's native aortic valve commissures. The prosthetic valve includes three flexible leaflets (not shown herein, but see again the above-mentioned Braido reference). Each of these leaflets basically extends between a respective pair of annularly adjacent ones of commissure posts 50. Left and right edge portions of each leaflet are respectively attached to the posts 50 in the pair of posts between which that leaflet extends. A lower edge portion of each leaflet is attached to bottom ring structure 60 below and between the posts 50 between which that leaflet extends. The upper edge of each leaflet is relatively free and is able to move toward and meet the upper edges of the other two leaflets to close the valve, or to move radially out away from those other two leaflet upper edges to open the valve. The direction of blood flow through the valve (when open) is upward as viewed in FIG. 1.

It should be noted that in FIG. 1 and in all other embodiments of this invention the bottom ring cell 62 immediately below each commissure post 50 is different from the other bottom ring cells 60. In particular, bottom ring cells 62 are stronger and more resistant to collapse (in a direction that is circumferential of the valve (left-right as viewed in FIG. 1)) than the other bottom ring cells 60. This greater strength of cells 62 accounts for the fact that even in the collapsed condition shown in FIG. 1, cells 62 remain relatively open, while all of the other cells 60 are very nearly closed in the circumferential direction. Indeed, the condition of cells 62 shown in FIG. 1 may also be very nearly the fully expanded condition of those cells. Most of the annular compression and re-expansion of bottom ring 60 may occur in cells other than cells 62, with cells 62 remaining at or nearly at the same size (in the circumferential direction) in both the collapsed condition and the re-expanded condition of the valve. Cells 62 can be given the above-described greater strength, for example, by increasing the width and/or thickness of the members that form those cells.

Figure 5:
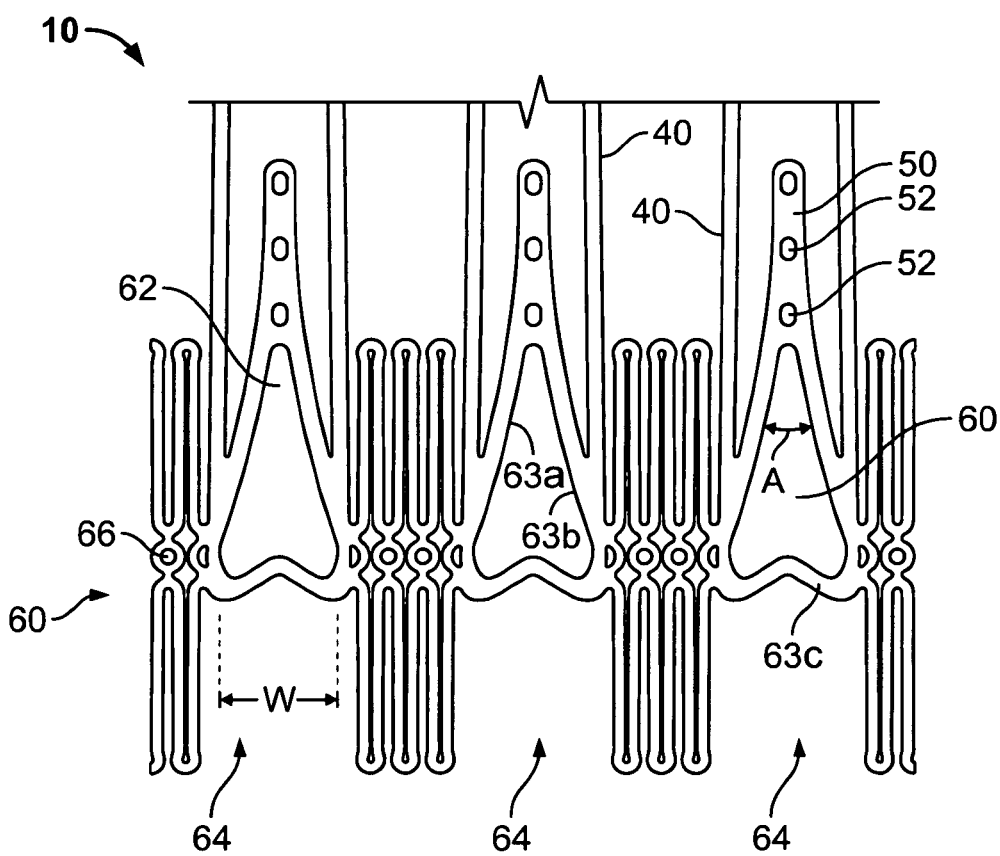
FIG. 5 shows another portion of what is shown in FIG. 1 on a larger scale.

To quantify the possible feature of the invention that has just been described, when a valve frame like 10 with this feature is subjected to an annular collapsing force that reduces annulus portion 20 to 50% of its full (expanded) size as an operating valve, each of cells 62 still preferably retains at least 75% of its full operating size width (e.g., as measured in the area indicated by the dimension W in FIG. 5). Note that each substructure that includes a commissure post 50 and a cell 62 may be described as a Y-shaped structure (with post 50 forming the base member of the Y, and with cell sides 63*a* and 63*b* forming the diverging arm members of the Y). The cell 62 of this Y-shaped structure is closed by a linking member 63*c* that interconnects the arm members 63*a* and 63*b* remote from where the arms begin to diverge from one another. The upper end of post 50 is a free end portion. The included angle A between diverging arm members 63*a* and 63*b* is preferably less than 90°. Dimension W is typical of how the open space between arms 63*a* and 63*b* can be measured. Linking member 63*c* may help to resist collapse of this open space; but, on the other hand, it may still allow some change in the size of the cell 62 for which it provides some of the perimeter structure.

The following summarizes some of the benefits and other features of the above-described approach. The increase in stiffness of commissure posts 50 and associated cells 62 can help to maintain repeat cycle deflection over time. (Such repeat cycle deflection may include deflection of posts 50 in the radial direction in response to each cycle of opening and closing of the valve after it has been implanted and is functioning in a patient.) Making parts 50/62 relatively non-collapsible and non-expanding facilitates configuring the geometry of those parts without major constraints in order to achieve a desired flexibility/stiffness balance (e.g., in the radial direction). Note that connecting struts 40 are directly attached to the flexing posts 50/62 to provide additional support and/or stiffness. The following further explains the mechanism of stent post flexibility/stiffness. This performance can be controlled by varying the contact point of the connecting arms 40 along the inverted Y post arms. For example, connecting struts 40 may be connected (1) at or near the tip of the posts 50 in one extreme possibility, (2) at or near the bottom of the inverted Y structure in the other extreme possibility, (3) or anywhere in between these two extremes. This can greatly increase or decrease the ability of the post tip to deflect inwardly. This is another way that the flexibility/stiffness can be controlled (in addition to changing the width and/or thickness of the inverted Y arms).

Another possibly advantageous feature that is illustrated by FIG. 1 is the absence of frame geometry and metal below each post 50 and cell 62. In other words, bottom ring 60 does not extend down below posts 50 nearly as far as it extends down elsewhere. The resulting recesses 64 (extending upwardly into the structure) help the implanted valve avoid interfering with the patient's adjacent mitral valve.

Each commissure post 50 has several eyelets 52 for easier leaflet integration (attachment).

Eyelets 30 in top ring cells 20 can be used to pass a wire (e.g., of nitinol) or other tether through frame 10 and then through a central lumen of the delivery system. This aids in reducing the expanded top (aortic) ring diameter for retrieval of the valve for purposes of repositioning or removing the valve. In other words, the above-mentioned tether(s) through eyelets 30 can be tensioned to pull eyelets 30 and adjacent frame elements radially inwardly so that they will again fit into a delivery system sheath. For example, the above-described tether and eyelet 30 structure can also help to prevent the stent 10 from catching on an edge of a sheath that is part of the delivery apparatus as mentioned above. Once the frame 10 is thus back in the delivery system, that system can be used to reposition and redeploy the valve, or alternatively to completely remove the valve from the patient.

Figure 4:
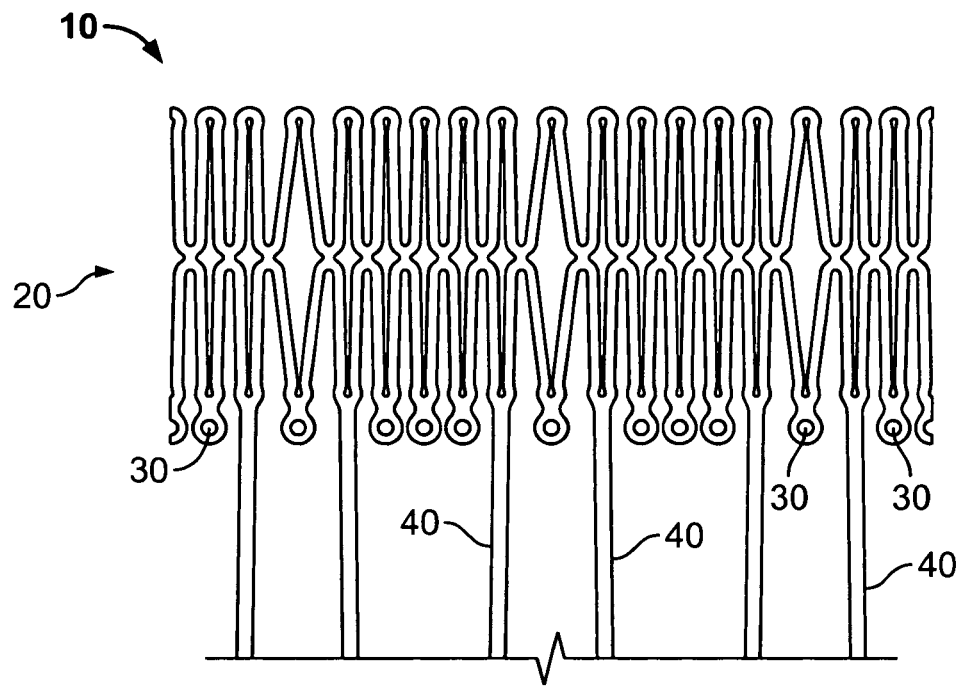
FIG. 4 shows a portion of what is shown in FIG. 1 on a larger scale.

As has been noted, FIG. 4 shows an enlargement of the upper portion of frame 10 from FIG. 1. FIG. 5 shows an enlargement of the lower portion of frame 10 from FIG. 1.

Figure 6:
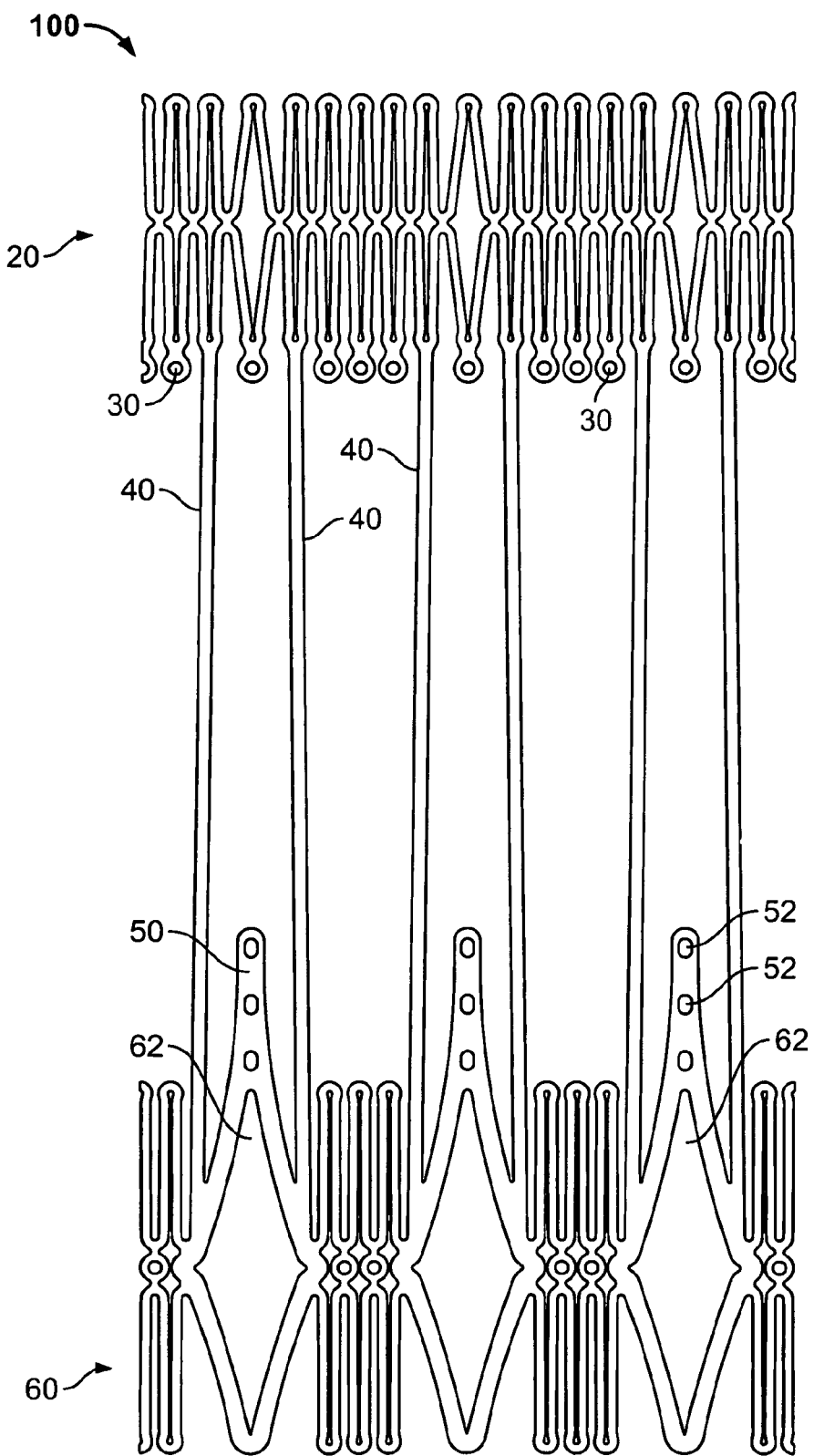
FIG. 6 is similar to FIG. 1 for another illustrative embodiment in accordance with the invention.

FIG. 6 is a view similar to FIG. 1 showing an alternative frame embodiment 100. The only difference between frame 10 and frame 100 is that in frame 100 cells 62 are diamond-shaped and extend down to or close to the plane containing the bottoms of other bottom (annulus portion) ring cells 60. (The same reference numbers are used in FIGS. 1 and 6 for elements that are the same or similar.) This means that frame 100 does not include the upwardly extending recesses 64 that are shown in earlier FIGS. and described above for frame 10.

Figure 7:
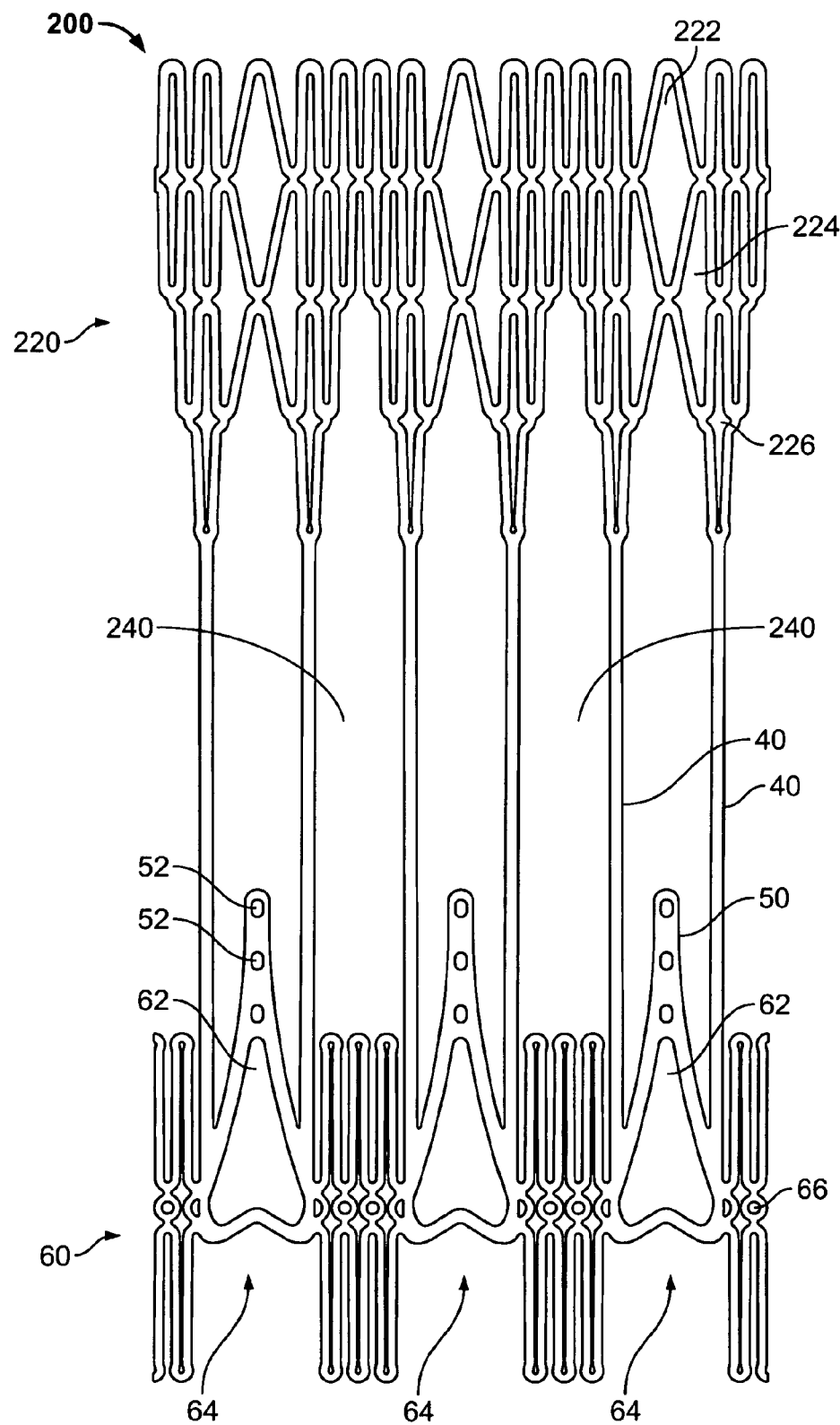
FIG. 7 is similar to FIG. 6 for yet another illustrative embodiment in accordance with the invention.

FIG. 7 shows an illustrative embodiment of possible further features in accordance with the invention. Again, these features can help to facilitate easy repositioning and/or retrieval of the valve. FIG. 7 is another view similar to FIGS. 1 and 6, but FIG. 7 shows a modified frame embodiment 200. Elements in FIG. 7 that are the same as or similar to elements in earlier FIGS. have the same reference numbers again in FIG. 7. In particular, the differences from frame 10 are in top ring area (aortic portion) 220.

As shown in FIG. 7, the top ring 220 cell design is such that there are no elbow struts that can catch on a sheath of delivery apparatus during valve collapsing. This is achieved by connecting all expandable cells in top ring 220 down to the six connecting struts 40 in a tapered manner. More specifically, the lower-most points or elbows 223a (FIG. 9) of the top-most row of cells 222 also form the side mid-point nodes of cells 224 in a next-lower row of the top ring. The lower-most points or elbows 225a of cells 224 form the side mid-point nodes of cells 226 in a still lower row of the top ring. The lower-most points or elbows 227a of cells 226 blend into (i.e., are the attachment points for) struts 40. As a consequence of this, no cell 222, 224, or 226 in top ring 220 has a downwardly projecting elbow that is exposed (i.e., does not smoothly blend into some further, lower structure, ultimately leading smoothly into struts 40). There are thus no exposed, downwardly pointing elbows on any top ring cells that could catch on a sheath that is moving (from below as indicated by arrow 203 in FIG. 8) back up over the top ring structure in order to re-collapse that structure for repositioning or retrieval of the valve.

Figure 8:
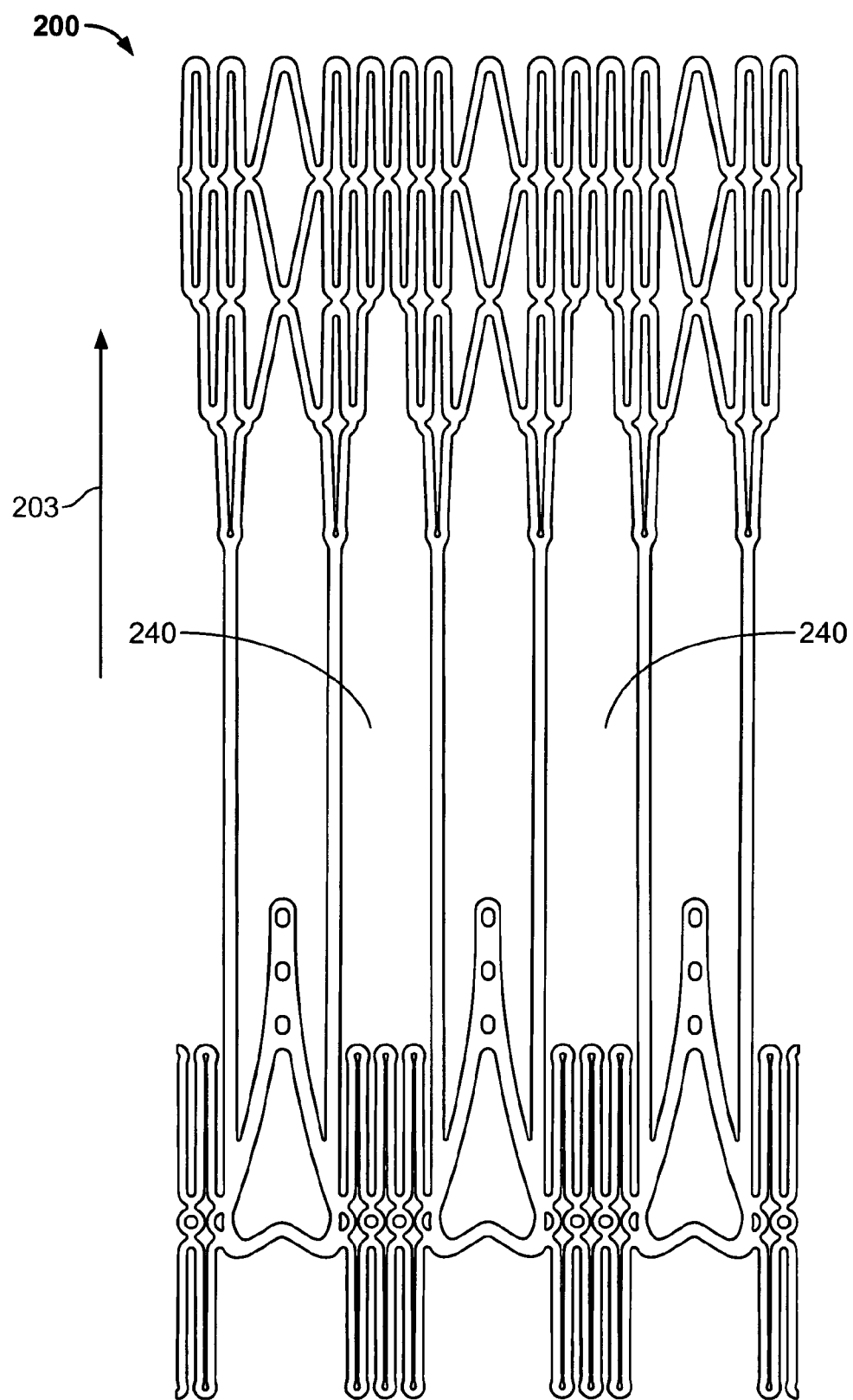
FIG. 8 repeats FIG. 7 with some additional reference information added to facilitate explanation of certain possible aspects of the invention.
Figure 9:
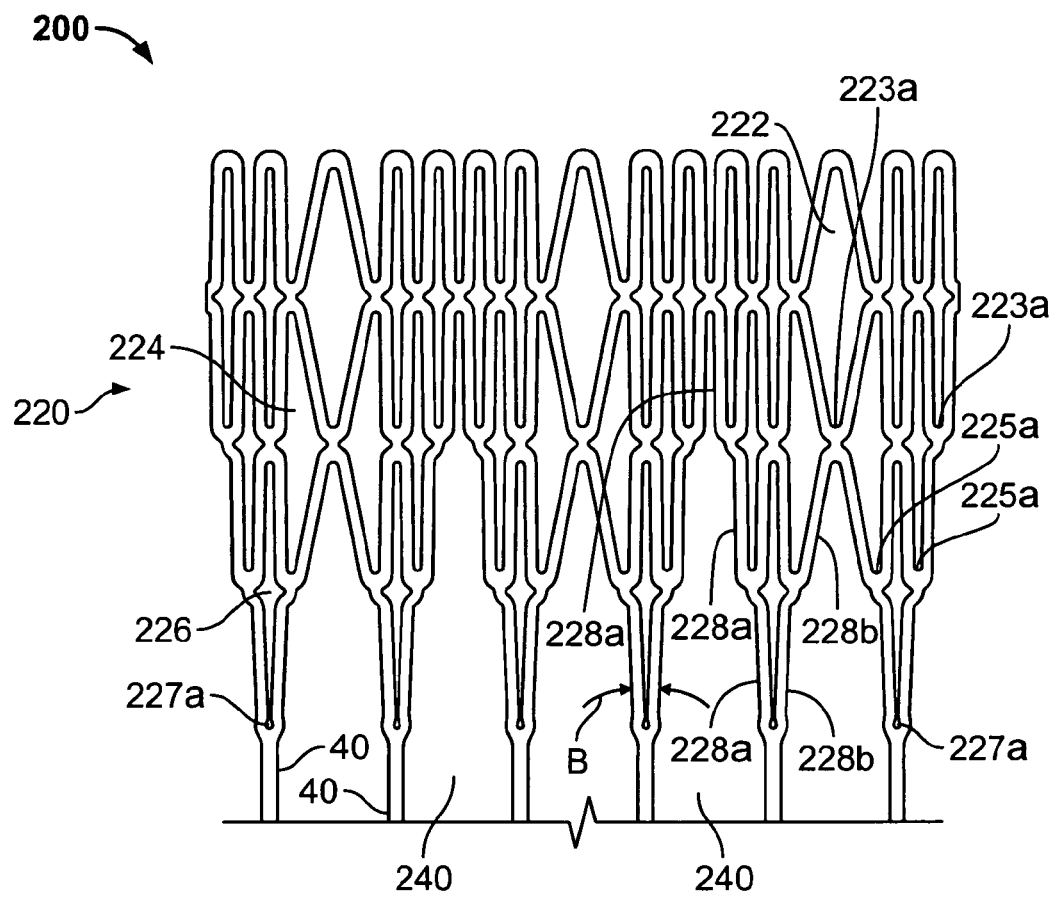
FIG. 9 shows a portion of what is shown in FIG. 8 on a larger scale.

Another way to describe the feature illustrated by FIGS. 7-9 is to start from struts 40 and work upward. The upper end 227a of each strut 40 is the starting point for two arms (e.g., 228a and 228b) that diverge from one another as one proceeds upwardly from that starting point. The included angle B between these two arms is preferably less than 90°. Each of these arms 228a/b continues upwardly until it meets and joins the circumferentially (or annularly) adjacent arm 228a/b extending upwardly from another circumferentially (or annularly) adjacent one of the starting points 227a. There is no structure between any of the circumferentially adjacent arms 228 that emanate from circumferentially adjacent ones of starting points 227a. Thus there is no such structure that can catch on delivery apparatus that is moving upwardly (arrow 203 in FIG. 8) to re-collapse and re-enclose the upper portion of frame 200. All of the structure of aortic ring 220 is either between the pairs of arms 228a/b that emanate from the same starting point 227a or upwardly beyond that structure. Struts 40 and arms 228a/b can thus act to smoothly feed all of aortic ring 220 back into delivery apparatus that is moving upwardly as indicated by arrow 203 in FIG. 8.

The same principle illustrated by FIGS. 7-9 can be alternatively or additionally applied to bottom ring structure (annulus portion) 60 for the reverse deployment option (i.e., deployment of annulus portion 60 first). In other words, bottom ring cells 60 (other than 62 and posts 50) can be blended into connecting struts 40 via one or more intervening rows of additional bottom ring cells to avoid exposed, upwardly facing elbows (other than posts 50).

Figure 14:
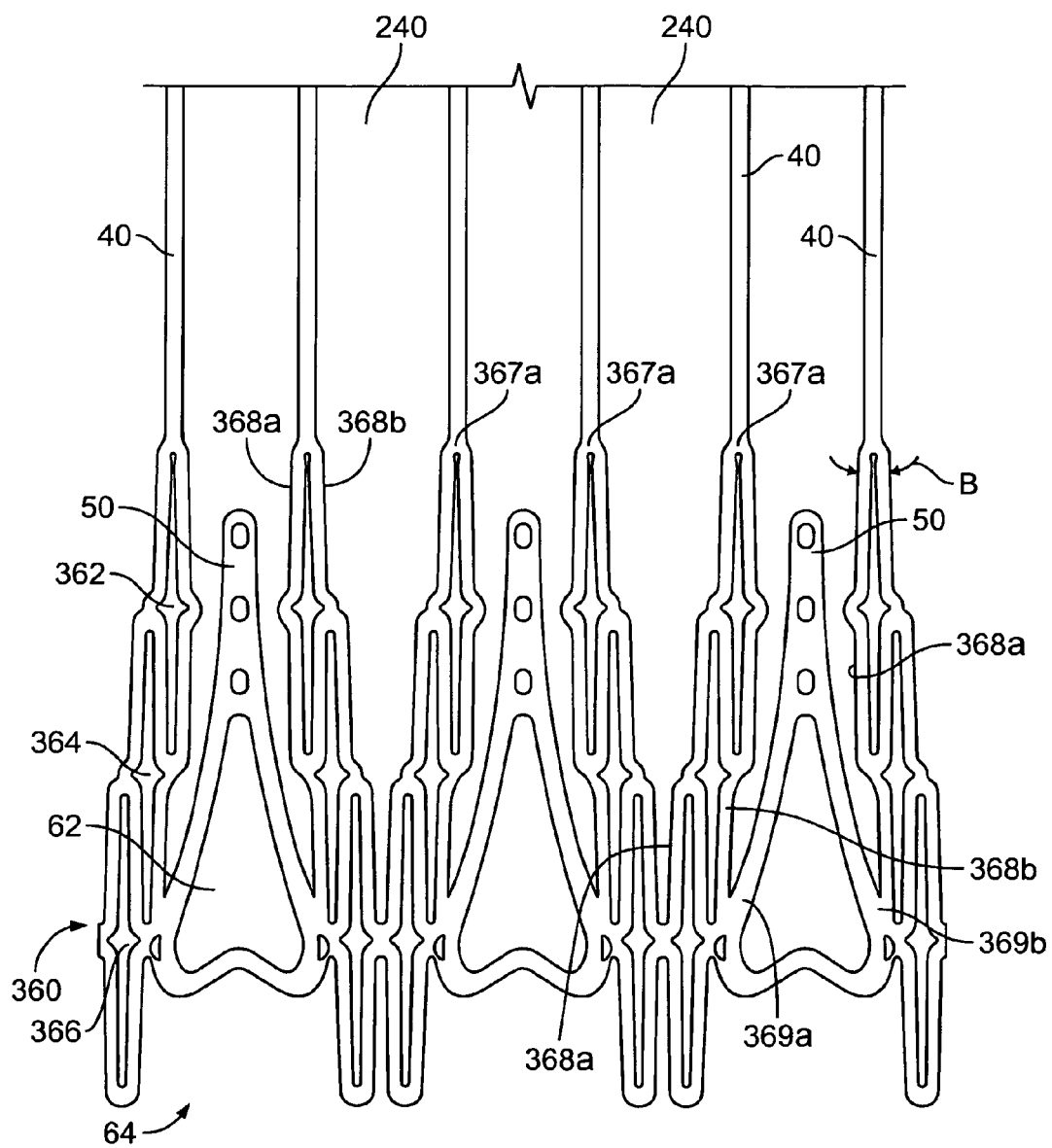
FIG. 14 is similar to FIG. 5 for another illustrative embodiment of the invention.
Figure 15:
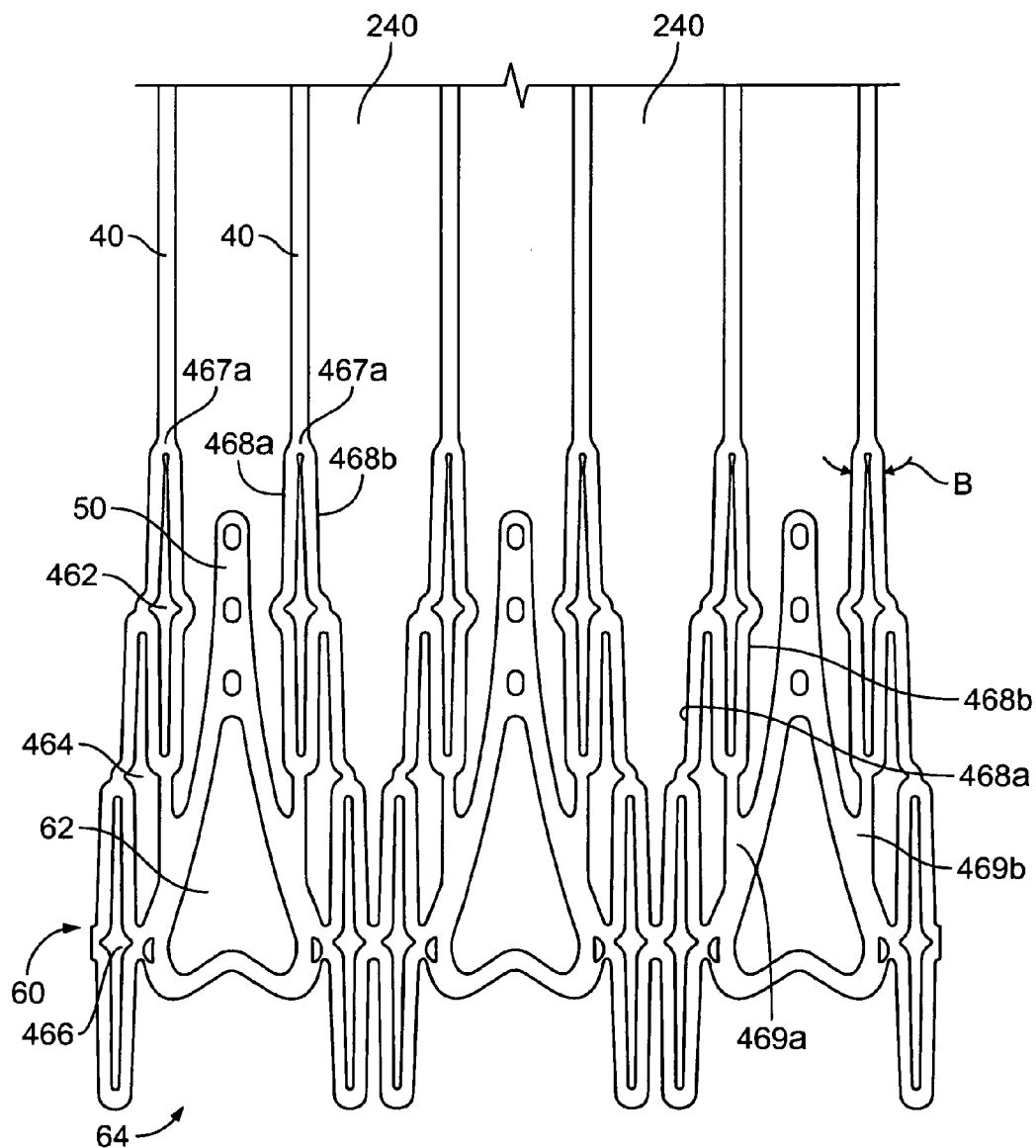
FIG. 15 is similar to FIG. 14 for still another illustrative embodiment of the invention.

The point mentioned in the immediately preceding paragraph is illustrated by FIGS. 14 and 15 (which show two different illustrative embodiments). In FIG. 14 annulus portion 360 includes three rows or tiers of closed-perimeter, open-center cells 362, 364, and 366. All of the cells 362 in the topmost row begin (at their upper ends) at points 367a that are at the bottom ends of struts 40. The rows of cells 364 and 366 below top row 362 fan out gradually from the topmost row, so that no cell in any row has an upwardly pointing corner that is not also part of the side structure of another cell that is higher up. In other words, from each starting point 367a, two arms 368a and 368b gradually diverge and continue relatively smoothly down as far as is necessary to include the upper elbows of all cells 362, 364, and 366 that are between those arms. All cells in annular portion 360 are between some such pair of diverging arms 368a and 368b. (Again, the included angle B between each such pair of arms 368a and 368b is less than 90°.) Avoidance of exposed, upward-pointing cell corners in this way facilitates reintroduction of annulus portion 360 into a downwardly moving delivery apparatus sheath in the event that the prosthetic valve must be repositioned in the patient or withdrawn from the patient. The only upwardly pointing structures that are not thus prevented from being exposed are commissure posts 50. However, these posts 50 can be designed to have a slight inward tilt toward the central axis, which can help prevent a frame-collapsing sheath from catching on these posts as the sheath passes over them.

Again it is emphasized that the principles illustrated by FIGS. 7-12 (i.e., no exposed cell corners in aortic portion pointing toward annulus portion) and FIGS. 14 and 15 (i.e., no exposed cell corners in annulus portion pointing toward aortic portion) can be combined in one valve frame in accordance with this invention.

FIG. 15 shows an alternate embodiment of what is shown in FIG. 14. Reference numbers in FIG. 15 in the 400 series that are otherwise similar to reference numbers in FIG. 14 in the 300 series refer to similar elements. The description of FIG. 15 can therefore be somewhat abbreviated because the description of FIG. 14 applies again to FIG. 15 with only the above reference number difference. The major difference between FIGS. 14 and 15 is in where the cellular structure of the annulus portion connects to the structure of commissure post cells 50/62. In FIG. 14 the upper-most of these connection points 369a/b are relatively close to the bottom of cells 62. In FIG. 15, on the other hand, the upper-most of these connection points 469a/b are closer to the tops of cells 62. As is pointed and described elsewhere in this specification, this kind of variation can be used to affect the stiffness of the commissure posts structures 50/62. For example, all other things being equal, the commissure post structures 50/62 in FIG. 14 tend to be more flexible (e.g., for deflection radial of the prosthetic valve) than the commissure post structures 50/62 in FIG. 15. The length of cantilevering of the structure 50/62 is greater in FIG. 14 than in FIG. 15.

Figure 10:
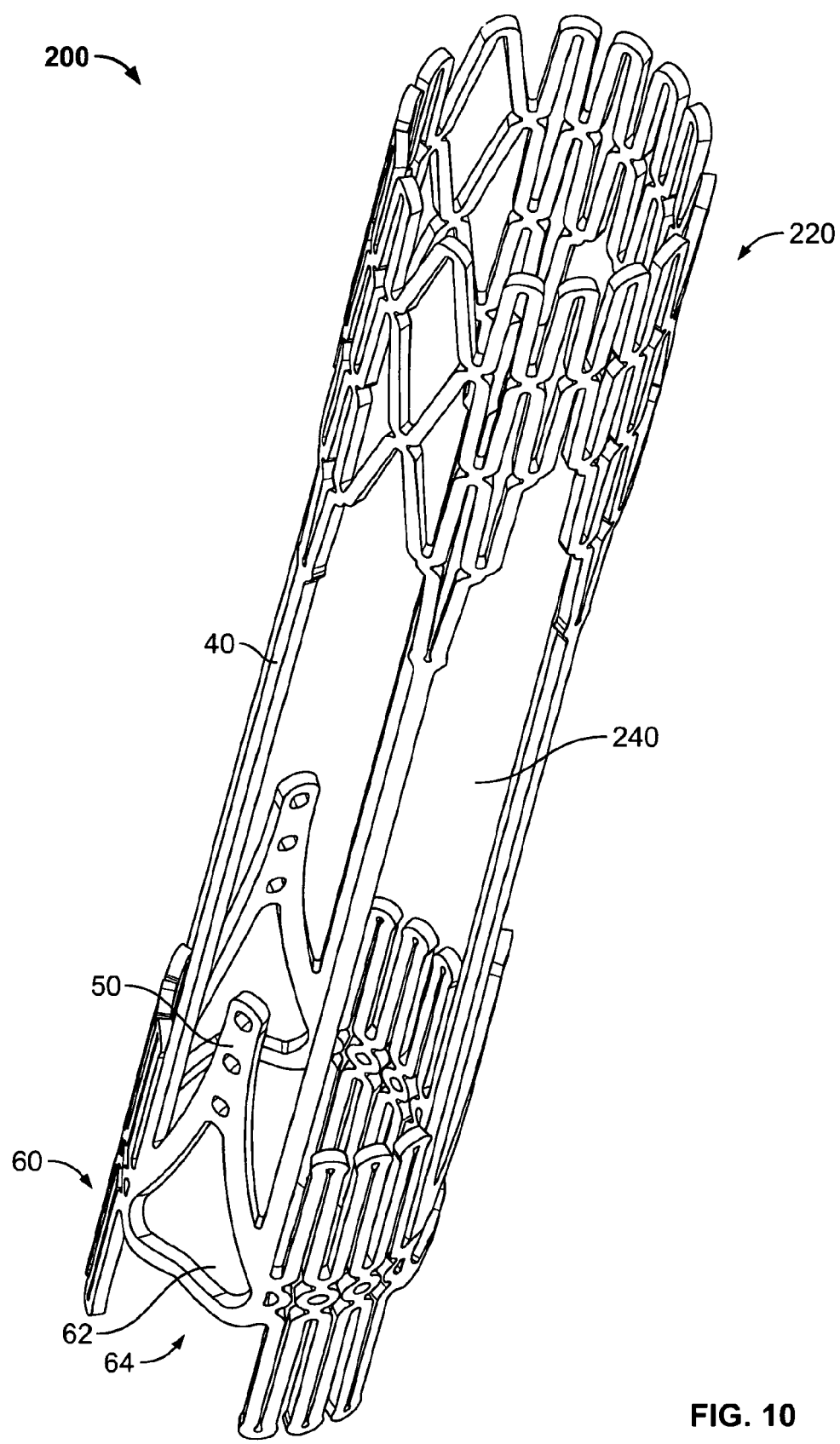
FIG. 10 is a simplified perspective or isometric view of apparatus of the type that is shown in FIG. 8.
Figure 11:
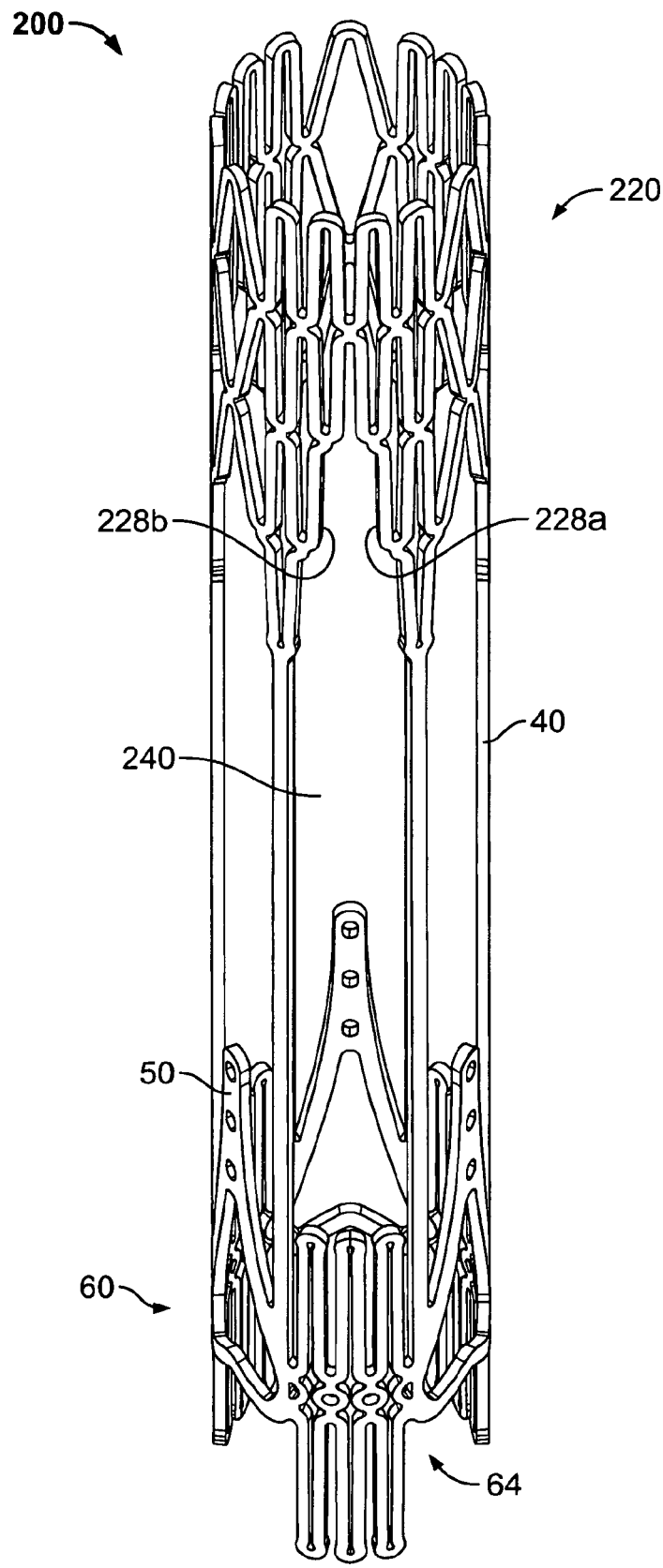
FIG. 11 is similar to FIG. 10 from another angle.
Figure 12:
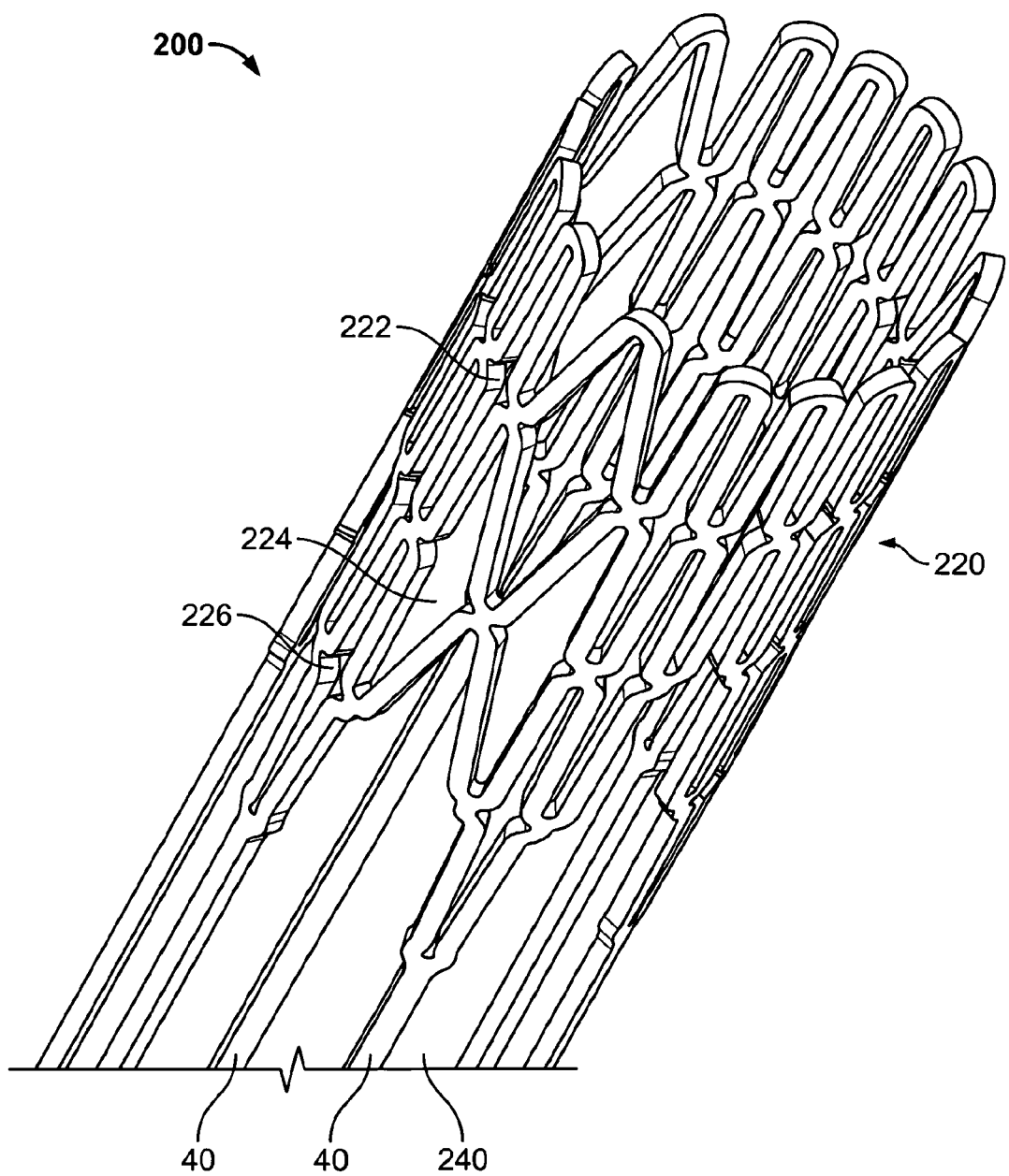
FIG. 12 is similar to a portion of FIGS. 10 and 11 from still another angle.
Figure 13:
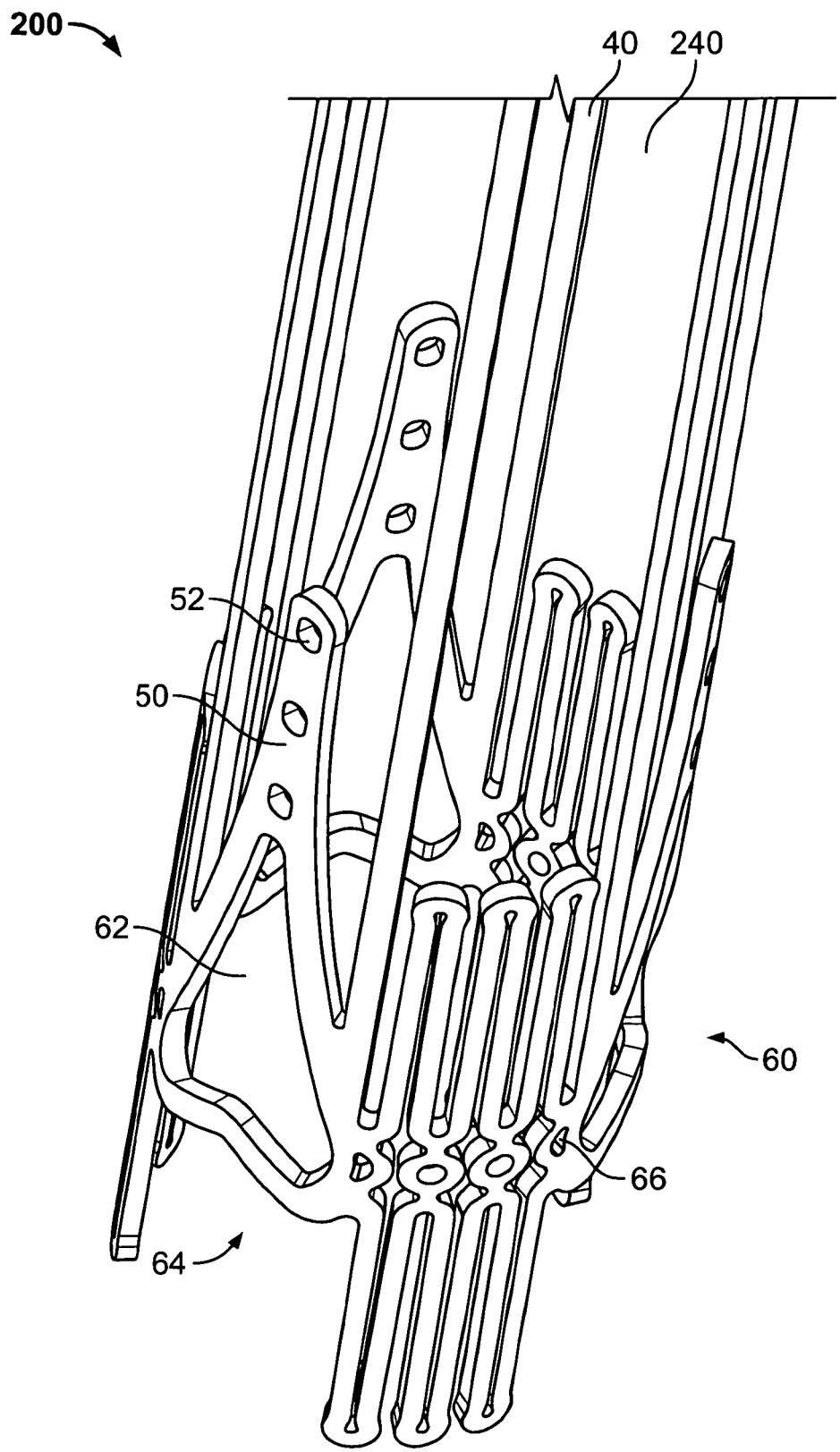
FIG. 13 shows a portion of what is shown in FIG. 10 on a larger scale.

FIGS. 10 and 11 show frame 200 in the round, but still in the collapsed condition. FIG. 12 shows an enlargement of the upper portion of what is shown in FIGS. 10 and 11. FIG. 13 shows an enlargement of the lower portion of what is shown in FIGS. 10 and 11.

The following paragraphs highlight various aspects of the invention.

Flexible stent frame posts 50 separated from the main frame structure on the upper or blood outflow end, but attached to the stent structure at the lower or blood inflow end of the posts. This allows the stent (especially posts 50) to flex and deflect to accommodate valve tissue function in the open/closed cycles.

At least three non-expanding stent post members 50/62. This allows for balancing the stiffness of the bending/flexing post 50/62 by dialing in geometry of the post as well as the width of its struts (i.e., the side members of cells 62).

At least three connecting members 40 that connect the stent's top (outflow) expanding ring geometry 20/220 with the stent's bottom (inflow) expanding ring geometry 60.

The connecting struts 40 can be attached to the stent's posts 50/62 at various locations to provide additional means of adjusting stiffness, as well as controlling stent post 50/62 flexibility and deflection.

Connecting struts 40 can also be attached to any of the bottom cells. More than six connecting struts 40 are also possible if it is desired to connect every cell at the top ring with every cell at the bottom ring. The geometries of the connections between top and bottom rings can vary significantly, but the objective is to eliminate exposed elbows that can potentially cause catching when re-sheathing.

A unique and differentiated top ring geometry 220 design that includes several struts (cell perimeter members) and closed and open cells that are disposed in rows 222, 224, and 226. As the rows approach the connecting struts 40, the number of cells and struts (cell perimeter members) decreases in a manner that forms a smooth and streamed transition from the very top (outflow end) down to the point of making connection with the six struts 40. The geometry is such that there are no exposed strut (cell perimeter member) elbows that are not connected to the remainder of the geometry such that they can catch and hang on the edge of an advancing sheath during re-sheathing for repositioning or for retrieval.

The same geometry described in the above paragraph can be applied to the stent's bottom ring 60 (e.g., as shown in FIGS. 14 and 15).

This stent invention can incorporate the above-described geometry on the top ring only, the bottom ring only, or on both rings. With incorporation on the top ring only, the sheath can only be advanced from the blood inflow to the blood outflow end of the stent when recapture is desired. Similarly, if the geometry is incorporated on the bottom ring only, the sheath can only be advanced from the blood outflow to the blood inflow end of the stent. Finally, if the geometry is incorporated on both rings, the sheath can be advanced from either direction when stent collapsing for recapture is desired.

The geometry design described above can vary in strut (e.g., cell perimeter member) width, thickness, shape, taper, and/or length to create a desired balance for that geometry that will allow for reduced strain during initial processing expansion, collapsing, and re-expansion. Therefore, the design can utilize various combinations of these variations to achieve the right balance.

The mid-section 40 of the stent between the top and bottom rings can be designed to expand to fit and self-anchor in the valve sinus area (i.e., the valsalva sinus). Also, it can be designed with no curves (straight members 40) and serve the purpose of connecting the stent's top and bottom rings. Finally, it can be designed to have predetermined bends that may have some functional aspects when collapsed for delivery, as well as in the deployed functional state.

The stent geometry incorporates several eyelet designs (e.g., 30) that are disposed at various locations of the stent. Depending on their locations, these eyelets serve different functions. When disposed around the top ring 20/220, they can facilitate stent collapsing for certain stent geometry designs by threading a temporary thin nitinol wire suture or other appropriate tether member to loop through the eyelet(s) 30 and back into the central lumen of delivery apparatus. When the stent is partially deployed and recapture is desired, the wires can be pulled proximally, which causes the geometry to taper and "funnel" radially inwardly into the delivery system sheath (tube).

The stent posts 50 can incorporate eyelets 52 to facilitate leaflet integration and attachment to the posts with appropriate means (e.g., with sutures).

The stent's bottom (inflow) ring 60 geometry may also incorporate eyelets 66 at various locations that can be utilized for leaflet integration, cuff integration, or for attaching members that can assist in re-collapsing the valve during repositioning and retrieval.

The eyelets or other similar apertures can be disposed at different locations and in various combinations for purposes such as stent/tissue/cuff integration and/or stent deployment/ recapture/repositioning. Therefore, eyelets can be located at the corners of cells, or between cells at the top and bottom rings, or anywhere in between.

The stent geometry at both the inflow and outflow edges can incorporate additional anchoring features so the stent remains secured during the cardiac cycle.

The stent frame has sections designed to allow clearance of the coronary arteries, thus not obstructing critical blood flow to the heart. This aspect of the invention is illustrated by reference numbers 240 in FIGS. such as FIGS. 7-15. When the valve frame opens up (expands annularly) at the implant site in the patient, these areas 240 between struts 40 will become relatively large, open, and unobstructed areas. If posts 50 are aligned with the patient's native valve commissure posts, open areas 240 (which are circumferentially offset from posts 50) will tend to be aligned with the patient's native coronary artery ostia. This helps to ensure that no part of the prosthetic valve blocks blood flow from the aorta into the coronary arteries. This property of the prosthetic valve is enhanced by the use of a design (e.g., like that shown in FIG. 7) in which one or both ends (upstream and/or downstream) of areas 240 are free of exposed cell elbows as described elsewhere in this specification. For example, there are no exposed, upstream-pointing cell elbows or corners between the arms that are labelled 228a and 228b in FIG. 11. This helps to keep the area that is labelled 240 in FIG. 11 open for avoidance of obstruction of a patient's coronary artery ostia.

The stent can incorporate a collapsible cuff to promote tissue in-growth, thus preventing perivalvular leaks.

The cell elbow geometry can incorporate unique geometry that stress-relieves the stent, as well as allowing for larger cell expansion and providing locations that can be used for leaflet and cuff integration.

The stent geometry design can have features (e.g., recesses 64) to relieve impingement on the mitral valve when expanded within calcified leaflets.

It will be understood that the foregoing is only illustrative of the principles of the invention, and that various modifications can be made by those skilled in the art without departing from the scope and spirit of the invention. For example, the number of closed-perimeter, open-centered cells (e.g., 20 or 60) that is used to form each ring of such cells can be more or less than the numbers shown in the accompanying FIGS. Similarly, the number of rows or tiers of such cells (e.g., 20 or 60) that are used in the aortic or annulus portions of frame 10, 100, or 200 can be different from the numbers shown in the accompanying FIGS.

The invention claimed is:

1. A frame structure for a prosthetic heart valve comprising:
a plurality of Y-shaped structures disposed in an annular array in which the Y-shaped structures are spaced from one another in a direction that is annular of the array, each of the Y-shaped structures including a base member having a first free end portion and an opposite second end to which a first end of each of two arms of the Y-shaped structure is connected, the arms of each of the Y-shaped structures diverging from one another in a direction away from the second end to define a space between the arms, the space extending in the annular direction; and
a plurality of connecting structures, each connecting structure extending between a respective pair of annularly adjacent ones of the Y-shaped structures, each connecting structure interconnecting the Y-shaped structures in the associated pair, each connecting structure being collapsible and re-expandable in the annular direction, each of the Y-shaped structures being sufficiently strong to maintain at least 75% of the space between its arms when the array is subjected to an annular collapsing force that collapses the array to 50% of an initial annular size,
wherein the arms of the Y-shaped structures are not shared by any of the connecting structures.

2. The frame structure defined in claim 1 wherein each of the connecting structures is connected to the arms of the Y-shaped structures in the associated pair but not to the base members of those Y-shaped structures.

3. The frame structure defined in claim 1 wherein each of the Y-shaped structures further includes a linking member that interconnects the arms of the Y-shaped structure at a location that is spaced from the second end.

4. The frame structure defined in claim 1 wherein the array lies in an approximately tubular geometric space that surrounds a central longitudinal axis, and wherein the base member of each of the Y-shaped structures is approximately parallel to the longitudinal axis.

5. The frame structure defined in claim 4 wherein all of the first free end portions point in a first direction parallel to the longitudinal axis.

6. The frame structure defined in claim 5 wherein the first free end portions all extend farther in the first direction than any portions of any of the connecting structures.

7. The frame structure defined in claim 6 wherein no portions of any of the Y-shaped structures extend as far opposite the first direction as portions of the connecting structures.

8. The frame structure defined in claim 7 wherein each of the Y-shaped structures further includes a linking member that interconnects the arms of the Y-shaped structure at a location that is spaced from the second end.

9. The frame structure defined in claim 6 wherein each of the Y-shaped structures further includes a linking member that interconnects the arms of that Y-shaped structure at a location that is spaced from the second end.

10. The frame structure defined in claim 9 wherein the linking member of each of the Y-shaped structures extends approximately as far opposite the first direction as portions of the connecting structures.

11. The frame structure defined in claim 5 further comprising:
an aortic portion that is spaced from the Y-shaped structures and the connecting structures in the first direction, the aortic portion being annular about the longitudinal axis and being annularly collapsible and re-expandable; and
a plurality of strut members for attaching the aortic portion to the Y-shaped and connecting structures of the frame structure.

12. The frame structure defined in claim 11 wherein the aortic portion comprises:
a plurality of open-centered, closed-perimeter cells disposed in an annular array in which connection points between annularly adjacent cells are at intermediate points along sides of the cells and each cell includes first and second ends that respectively point in the first direction and opposite the first direction.

13. The frame structure defined in claim 12 wherein the second end of each of the cells includes an eyelet for attaching a tether member that can be used to pull the eyelet radially in toward the central longitudinal axis.

* * * * *